United States Patent [19]

Zaiger et al.

[11] Patent Number: Plant 5,624

[45] Date of Patent: Jan. 7, 1986

[54] PLUM TREE ("AUTUMN GIANT")

[76] Inventors: Chris F. Zaiger, 537 Rosemore Ave.; Gary N. Zaiger, 1907 Elm Ave.; Leith M. Gardner, 1207 Grimes Ave.; Grant G. Zaiger, 2121 Elm Ave., all of Modesto, Calif. 95351

[21] Appl. No.: 602,064

[22] Filed: Apr. 19, 1984

[51] Int. Cl.[4] ..... A01H 5/00

[52] U.S. Cl. ..... Plt./38

[58] Field of Search ..... Plt./38

*Primary Examiner*—James R. Feyrer

*Attorney, Agent, or Firm*—Roger B. Webster

[57] ABSTRACT

A new and distinct variety of plum tree which is of large size, vigorous, medium dense, and upright in growth; foliated with medium size, mostly elliptical leaves having a crenate margin; blooms from plump, free buds of medium size and length; and is a regular and productive bearer of very large, firm, red-blushed, yellow-flesh, semi-freestone fruit.

1 Drawing Figure

BACKGROUND OF THE VARIETY

FIELD OF THE INVENTION

In the field of plant genetics we conduct an extensive and continuing plant breeding program including the origination and asexual reproduction of orchard trees, and of which plums, peaches, and apricots are exemplary. It was against this background of our activities that the present variety of plum tree was originated and asexually reproduced by us in an experimental orchard located near Modesto, Stanislaus County, Calif.

CLASSIFICATION OF THE VARIETY

The present new and distinct variety of plum tree is embraced by Class 38, plants, of the United States Patent Office MANUAL OF CLASSIFICATION.

PRIOR VARIETIES

Among the existent varieties of plum trees which are known to us, and mentioned herein, are Santa Rosa and King David (both unpatented), and Roysum (U.S. Plant Pat. No. 2,619).

ORIGIN OF THE VARIETY

The present variety of plum tree was originated by us, in the aforesaid experimental orchard, as a selection from a large number of first generation seedlings from a cross between the King David and the Roysum. Such seedlings were planted and grown under careful and continuing observation, and one such seedling—which is the present variety—evidenced, in maturity, especially novel and desirable characteristics, and hence—because of its commercial potential—was selected for asexual reproduction.

ASEXUAL REPRODUCTION OF THE VARIETY

The present variety of plum tree was asexually reproduced, in the aforesaid experimental orchard, by budding, and such reproductions ran true to the original tree and its fruit in all respects.

SUMMARY OF THE VARIETY

The present variety of plum tree is, characteristically, of large size, vigorous, medium dense, and upright in growth; foliated with medium size, mostly elliptical leaves having a crenate margin; blooms from plump, free buds of medium size and length; and is a regular and productive bearer of very large, firm, red-blushed, yellow-flesh, semi-freestone fruit.

The present variety of plum tree is further characterized, in comparison to the Roysum, by bearing fruit at an earlier age, and which bearing usually initiates in the second growing season.

The present variety of plum tree is further characterized by blooming approximately nine days later than the Santa Rosa, and the fruit harvesting relatively late and approximately with the Roysum; the fruit being larger than that of the Roysum, and being blushed with a higher degree of red skin color.

The present variety of plum tree is still further characterized by fruit which is not susceptible to skin cracking or pre-harvest drop of immature fruit; the fruit being of good eating and long-distance shipping quality.

BRIEF DESCRIPTION OF THE DRAWING

The drawing comprises illustrations, by photographic reproduction in color, of typical specimens of the foliage and shipping-ripe fruit of the present variety of plum tree; such illustrations being of a twig with leaves, and separate fruit; one of the latter being cut in half to expose the flesh, with the stone remaining in one of the halves.

DESCRIPTION OF THE VARIETY

The botanical details of this new and distinct variety of plum tree—with color definitions (except those in common color terms) referenced to Reinhold Color Atlas by A. Kornerup and J. H. Wanscher—are as follows:

Tree:
- *Size.*—Large.
- *Vigor.*—Vigorous.
- *Growth.*—Upright.
- *Density.*—Medium.
- *Production.*—Productive.
- *Bearing.*—Regular.

Trunk:
- *Form.*—Stocky.
- *Texture.*—Medium.

Branches:
- *Form.*—Medium stocky.
- *Texture.*—Medium rough.
- *Lenticels.*—Number — Medium. Size — Medium.

*Color.*—Dark brown.

Leaves:

*Size.*—Medium. Length range — $4\frac{1}{2}''$ to $5\frac{1}{2}''$. Width range — $2\frac{3}{4}''$ to $3\frac{1}{4}''$.

*Shape.*—Mostly elliptical. Some oblanceolate.

*Petiole.*—Medium size. Average length — $\frac{1}{2}''$. Average thickness — 3/32".

*Glands.*—Number 1 to 4 — Average 2.

*Margin.*—Crenate.

*Color.*—Upper surface — Medium green (28-E-7 to 28-F-8). Lower surface — Lighter green (28-D-6 to 28-D-8).

Flower Buds:

*Size.*—Medium.

*Length.*—Medium.

*Form.*—Plump. Free.

Flowers:

*Blooming period.*—Date of first bloom — Mar. 2, 1983. Date of full bloom — Mar. 6, 1983. Blooms approximately nine days later than Santa Rosa.

Fruit:

*Maturity when described.*—Shipping ripe.

*Date of first picking.*—Sept. 20, 1983.

*Date of last picking.*—Sept. 26, 1983.

*Size.*—Very large. Normal range — Axial diameter $2\frac{1}{4}''$ to $2\frac{3}{4}''$. Normal range — Transverse in suture plane — $2\frac{1}{4}''$ to $2\frac{1}{2}''$. Normal range — Right angles to suture plane — $2\frac{1}{4}''$ to $2\frac{1}{2}''$.

*Form.*—Globose. Slightly variable.

*Suture.*—Usually pronounced from base to apex. Slightly deeper at base.

*Cavity.*—Rounded to slightly elongated in suture plane. Average depth — $\frac{3}{8}''$. Average breadth — $\frac{5}{8}''$.

*Base.*—Rounded to slightly retuse. Variable.

*Apex.*—Usually rounded. Varies from slightly depressed to raised pistil point.

*Stem.*—Average length — $\frac{1}{2}''$. Average width — 3/32".

Skin:

*Thickness.*—Medium.

*Texture.*—Medium.

*Tendency to crack.*—None.

*Down.*—Wanting.

*Bloom.*—Moderate to heavy.

*Color.*—Yellow undercolor (5-A-7 to 4-A-8). Red blush (9-B-8 to 10-A-8) covering a high degree of the surface.

Flesh:

*Texture.*—Firm. Meaty.

*Ripens.*—Evenly.

*Flavor.*—Mild.

*Eating quality.*—Good.

*Color.*—Yellow (5-A-5 to 5-A-6). Surface of pit cavity — Brownish yellow (5-C-5).

Stone:

*Type.*—Semi-freestone. Usually adheres to flesh along ventral edges, but variable from full free to nearly clingstone.

*Size.*—Average length — 1". Average width — 9/16". Average thickness — $\frac{3}{8}''$.

*Surface.*—Slightly furrowed. Ridges deeper near base.

*Sides.*—Nearly equal.

*Base.*—Straight.

*Apex.*—Acuminate.

*Form.*—Ovoid.

*Tendency to split.*—None.

*Color.*—Brown (7-C-4) to light brown (7-D-5).

Use: Market. Local and long distance shipping.

Keeping quality: Very good.

Shipping quality: Vergy good.

The plum tree and its fruit herein described may vary in slight detail due to climatic and soil conditions under which the variety may be grown; the present description being of the variety as grown in the Central Valley of California.

We claim:

1. A new and distinct variety of plum tree, substantially as illustrated and described, particularly characterized by usually initiating the bearing of fruit in the second growing season; by blooming approximately nine days later than Santa Rosa; by a relatively late harvest and which is approximately with the Roysum; and by bearing of very large, firm, yellow-flesh, semi-freestone fruit larger than the Roysum and blushed with a higher degree of red skin color; the fruit, which is not susceptible to skin cracking or preharvest drop of immature fruit, being of good eating and long-distance shipping quality.

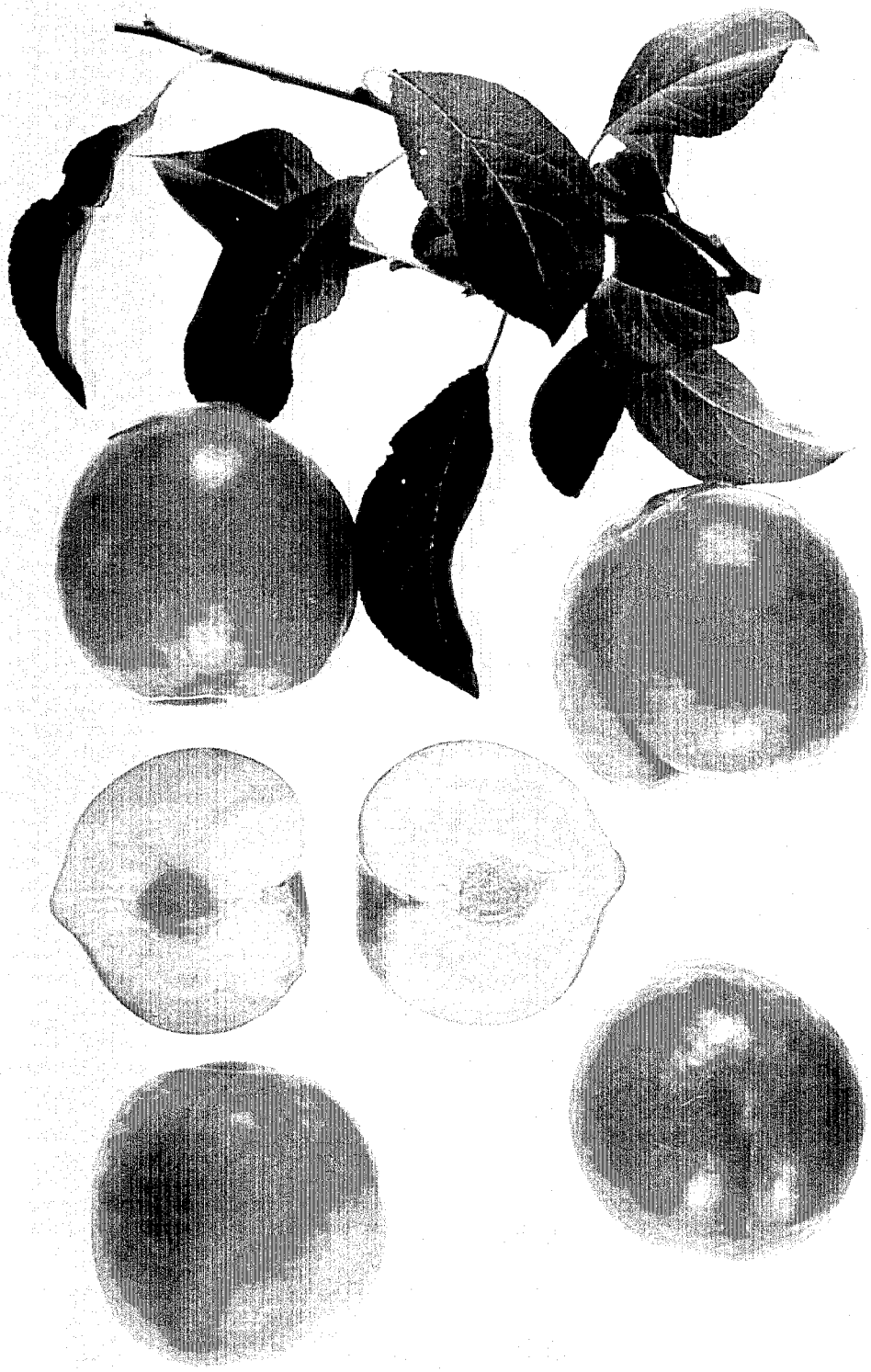

* * * * *